(12) United States Patent
Spartz et al.

(10) Patent No.: US 7,595,887 B2
(45) Date of Patent: Sep. 29, 2009

(54) MULTIGAS MONITORING AND DETECTION SYSTEM

(75) Inventors: Martin L. Spartz, Ellington, CT (US); Vidi Saptari, Cambridge, MA (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 12/119,244

(22) Filed: May 12, 2008

(65) Prior Publication Data

US 2008/0251727 A1 Oct. 16, 2008

Related U.S. Application Data

(63) Continuation of application No. 11/240,799, filed on Sep. 30, 2005, now Pat. No. 7,372,573.

(51) Int. Cl.
*G01B 9/02* (2006.01)
*G01J 3/45* (2006.01)

(52) U.S. Cl. ..................................................... 356/451

(58) Field of Classification Search ................. 356/244, 356/439, 451, 454, 480; 250/339.07–339.09, 250/339.11–339.13
See application file for complete search history.

(56) References Cited

U.S. PATENT DOCUMENTS

| | | | |
|---|---|---|---|
| 4,183,670 A | 1/1980 | Russell | |
| 4,538,910 A * | 9/1985 | Doyle | 356/451 |
| 5,341,207 A | 8/1994 | Tank et al. | |
| 5,440,143 A | 8/1995 | Carangelo et al. | |
| 5,457,316 A * | 10/1995 | Cohen et al. | 250/286 |
| 5,541,728 A | 7/1996 | Dierking | |
| 5,777,735 A | 7/1998 | Reagen | |

(Continued)

FOREIGN PATENT DOCUMENTS

WO WO 98/27416 6/1998

(Continued)

OTHER PUBLICATIONS

Heise, H.M. et al. "Calibration Method fro the Infrared-Spectrometric Trace Gas Analysis". Fresenius Journal of Analytical Chemistry. vol. 332, No. 4, Jan. 1985, pp. 397-400.*

(Continued)

*Primary Examiner*—Michael A Lyons
(74) *Attorney, Agent, or Firm*—Proskauer Rose LLP (57) ABSTRACT

A spectroscopic detection system is described for monitoring ambient air for toxic chemical substances. The system can be a compact, portable multiple gas analyzer capable of detecting and discriminating a broad range of chemical constituents including various nerve and blister agents as well as toxic industrial chemicals at low or sub part per billion (ppb) levels. The system minimizes false alarms (e.g., false positives or negatives), features high specificity, and can operate with response times on the order of a few seconds to a few minutes, depending on the application. The system can be an entirely self-contained analyzer, with a Fourier Transform Infrared (FTIR) spectrometer, a gas sample cell, a detector, an embedded processor, a display, power supplies, an air pump, heating elements, and other components onboard the unit with an air intake to collect a sample and an electronic communications port to interface with external devices.

16 Claims, 8 Drawing Sheets

U.S. PATENT DOCUMENTS

| | | | |
|---|---|---|---|
| 6,784,428 B2 | | 8/2004 | Rabolt et al. |
| 7,372,573 B2 | * | 5/2008 | Spartz et al. ................ 356/451 |
| 2003/0184733 A1 | * | 10/2003 | Kameoka .................... 356/73 |
| 2006/0066824 A1 | * | 3/2006 | Knappe et al. ................ 355/30 |

FOREIGN PATENT DOCUMENTS

WO    WO 00/07411    2/2000

OTHER PUBLICATIONS

Ragunathan, N. et al. "Gas chromatography with spectroscopic detectors". Journal of Chromatography A, 856 (1999), pp. 349-397.*

MKS Gas Analysis, "MultiGas Purity," 4 pages, Jun. 2004.

MKS Gas Analysis, "MultiGas 2030," 4 pages, Nov. 2004.

MKS Gas Analysis, "MultiGas 2030 HS," 4 pages, Aug. 2005.

MKS Gas Analysis, "Process Insight," 6 pages, Aug. 2005.

Smiths brochure #1, "Smiths Detection GasID Portable Gas & Vapor Identifier," 2 pages, 2004.

Smiths brochure #2, "Smiths Detection GasID Portable Gas & Vapor Identifier," 2 pages, 2005.

Gasmet, "Multicomponent On-line FTIR Gas Analysis," 11 pages (available prior to Sep. 30, 2005).

Gasmet, "Gasmet Dx-4000 Multicomponent FTIR Gas Analyzer," 2 pages (available prior to Sep. 30, 2005).

Gasmet, " Gasmet Dx-4015 Multicomponent FTIR Gas Analyzer," 2 pages (available prior to Sep. 30, 2005).

Thermo Electron Corporation Product Overview, "MIRAN SapphIRe Portable Infrared Ambient Analyzer," 4 pages (available prior to Sep. 30, 2005).

* cited by examiner

MULTIGAS MONITORING AND DETECTION SYSTEM

CROSS-REFERENCE TO RELATED APPLICATIONS

The present application is a continuation of prior application Ser. No. 11/240,799, filed on Sep. 30, 2005, the entire disclosure of which is incorporated by reference herein.

FIELD OF THE INVENTION

The invention generally relates to absorption spectrometers, and more particularly to detecting trace amounts of chemical warfare agents, toxic industrial chemicals, and other trace compounds that can be found in ambient air.

BACKGROUND OF THE INVENTION

Spectroscopy is the study of the interaction between electromagnetic radiation and a sample (e.g., containing one or more of a gas, solid and liquid). The manner in which the radiation interacts with a particular sample depends upon the properties (e.g., molecular composition) of the sample. Generally, as the radiation passes through the sample, specific wavelengths of the radiation are absorbed by molecules within the sample. The specific wavelengths of radiation that are absorbed are unique to each of the molecules within the specific sample. By identifying which wavelengths of radiation are absorbed, it is therefore possible to identify the specific molecules present in the sample.

Infrared spectroscopy is a particular field of spectroscopy in which, for example, the types of molecules and the concentration of individual molecules within a sample are determined by subjecting the sample (e.g., gas, solid, liquid or combination thereof) to infrared electromagnetic energy. Generally, infrared energy is characterized as electromagnetic energy having wavelengths of energy between about 0.7 μm (frequency 14,000 $cm^{-1}$) and about 1000 μm (frequency 10 $cm^{-1}$). Infrared energy is directed through the sample and the energy interacts with the molecules within the sample. The energy that passes through the sample is detected by a detector (e.g., an electromagnetic detector). The detected signal is then used to determine, for example, the molecular composition of the sample and the concentration of specific molecules within the sample.

One particular type of infrared spectrometer is the Fourier Transform Infrared (FTIR) spectrometer. They are used in a variety of industries, for example, air quality monitoring, explosive and biological agent detection, semiconductor processing, and chemical production. Different applications for FTIR spectrometers require different detection sensitivity to enable a user to distinguish between which molecules are present in a sample and to determine the concentration of the different molecules. In some applications, it is necessary to identify the concentration of individual molecules in a sample to within about one part per billion (ppb). As industrial applications require increasingly better sensitivity, optimization of existing spectroscopy systems and utilization of new spectroscopy components can enable system to repeatably and reliably resolve smaller and smaller concentrations of molecules in samples.

SUMMARY OF THE INVENTION

The invention, in various embodiments, features a spectroscopic detection system for monitoring and/or detecting toxic chemical substances in a gas sample, such as ambient air. The system can be a compact, portable multiple gas analyzer capable of detecting and discriminating a broad range of chemical constituents including various chemical warfare agents (CWAs), toxic organic compounds (TOCs), and toxic industrial chemicals (TICs) at low or sub part per billion (ppb) levels. The system minimizes false alarms (e.g., false positives or false negatives), features high specificity, and can operate with response times on the order of a few seconds to a few minutes, depending on the application.

In one embodiment, the system can be packaged as an unobtrusive, automated unit capable of being deployed in an air handling system of a building to provide a rapid sensitive threat alert sufficient to protect building occupants and also allow adaptive infrastructure systems to react to the presence of a contaminant. In one embodiment, the unit is an entirely self-contained analyzer, with a FTIR spectrometer, a gas sample cell, a detector, an embedded processor, a display, an air pump, power supplies, heating elements, and other components onboard the unit with an air intake to collect a sample and an electronic communications port to interface with other devices.

In one aspect, the invention features an apparatus capable of measuring a trace gas. The apparatus includes a source of a first beam of radiation and an interferometer receiving the first beam of radiation from the source and forming a second beam of radiation including an interference signal. A sample cell is in optical communication with the interferometer, and the sample cell includes a concave reflective field surface at a first end of the sample cell and a substantially spherical, concave reflective objective surface at a second end of the sample cell. The objective surface and the field surface are in a confronting relationship, and the objective surface includes a cylindrical component increasing coincidence of foci in at least one plane to maximize throughput of the second beam of radiation propagating through the sample cell via multiple reflections on each of the field surface and the objective surface. The apparatus also includes a flow mechanism establishing a flow of a sample of gas through the sample cell, a cooled detector in optical communication with the sample cell, and a processor in electrical communication with the cooled detector. The cooled detector receives the interference signal propagating through the sample in the sample cell, and the processor determines from the interference signal an absorption profile for a trace gas in the sample. The source, interferometer, sample cell, cooled detector and processor can be disposed in a housing.

In another aspect, the invention features a method of optically measuring a trace gas. The method includes providing a portable absorption spectrometer including a sample cell having a field surface at a first end and an objective surface at a second end in a confronting relationship to form a folded path, and flowing a sample of ambient air through the sample cell. The volume of the sample cell and the number of passes of a beam of radiation in the folded path can be optimized to maximize throughput of the beam of radiation propagating in the sample cell to detect a trace gas having a concentration of less than about 500 ppb in the sample of ambient air.

In still another aspect, the invention features a method of optically measuring a trace gas. The method includes providing an absorption spectrometer including a sample cell that is substantially air tight. The sample cell includes a field surface at a first end and an objective surface at a second end in a confronting relationship to direct a beam of radiation through the sample cell. A first signal of the beam of radiation propagating through a sample of ambient air is measured at a first pressure in the sample cell. The sample cell is pressurized with ambient air to a second pressure, and a second signal of the beam of radiation propagating through the sample of ambient air at the second pressure is measured. The first signal and the second signal are combined to determine a signal indicative of the presence of a trace gas.

In various embodiments, the first signal and the second signal can be combined to determine an absorption profile for the trace gas. In some embodiments, the beam of radiation can include an interference signal. In one embodiment, an absorption profile for the trace gas can be determined from the interference signal propagating through the sample in the sample cell. In one embodiment, by pressurizing the sample cell, the amplitude of the absorption profile of the trace gas can be increased relative to a baseline signal.

In yet another aspect, the invention features a method of removing a contaminant from an optical system. The method includes a determining a concentration of a contaminant in at least a sample region of an absorption spectrometer and heating the sample region to a decontamination temperature to remove the contaminant if the concentration of the contaminant exceeds a contamination value The concentration of the contaminant is monitored while heating the sample region, and the heating of the sample region can be abated or ceased when the concentration of the contaminant reaches a decontamination value.

In still another aspect, the invention features an apparatus capable of measuring a trace gas. The apparatus includes an interferometer receiving the first beam of radiation from a source and forming a second beam of radiation comprising an interference signal, a sample cell in optical communication with the interferometer, a flow mechanism establishing a flow of a sample of gas through the sample cell, a module to heat at least the sample cell, a detector in optical communication with the sample cell, and a processor in electrical communication with the detector and the module. The detector receives the interference signal propagating through the sample in the sample cell. The processor determines from the interference signal a concentration of a contaminant in the sample, signals the module to heat the sample cell to a decontamination temperature to remove the contaminant if the concentration of the contaminant in the sample cell exceeds a contamination value, monitors the concentration of the contaminant while the module heats the sample cell, and signals the module to abate or cease heating the sample cell if the concentration of the contaminant reaches a decontamination value.

In other examples, any of the aspects above, or any apparatus or method described herein, can include one or more of the following features. In various embodiments, the trace gas has a concentration of less than about 500 ppb. In one embodiment, the trace gas has a concentration of between about 10 ppb and about 50 ppb. In one embodiment, the housing is portable and defines a hole for intake of ambient air comprising the sample of gas. The hole can be in fluid communication with the sample cell. In one embodiment, the sample cell can have a volume of less than about 0.8 liters. In some embodiments, the sample cell can have a pathlength of between about 5 meters and about 12 meters. In one embodiment, the apparatus also includes a heating element disposed in the portable housing to heat at least the sample cell to a temperature of between about 40° C. and about 180° C.

In some embodiments, the housing is mountable in an air handling system for a building. An alarm can sound to alert to the presence of a contaminant in the air handling system.

In one embodiment, the sample of gas flows through the sample cell at a rate of greater than about 3 liters per minute. The sample cell can have a gas exchange rate of between about 80% and about 95% in an interval of time of about 10 seconds. In one embodiment, the sample of gas includes a chemical warfare agent, a toxic inorganic compound, or a toxic organic compound. The apparatus can have a response time of less than about 20 seconds for about 50 ppb of a gas such as sarin, tabun, soman, sulfur mustard, or VX.

In various embodiments, a first absorption spectrum can be measured at a first resolution to detect the trace gas, and a second absorption spectrum can be measured at a higher resolution. In some embodiments, a first absorption spectrum can be measured at a first sensitivity to detect the trace gas, and a second absorption spectrum can be measured at a higher sensitivity.

In various embodiments, the field surface can include a concave reflective surface and the objective surface can include a substantially spherical, concave reflective surface. The objective surface can include a cylindrical component increasing coincidence of foci in at least one plane to maximize throughput of the beam of radiation propagating through the folded path of the sample cell. In one embodiment, an absorption profile for the trace gas can be determined from an interference signal propagating through the sample in the sample region.

Other aspects and advantages of the invention will become apparent from the following drawings, detailed description, and claims, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE INVENTION

Figure 1:
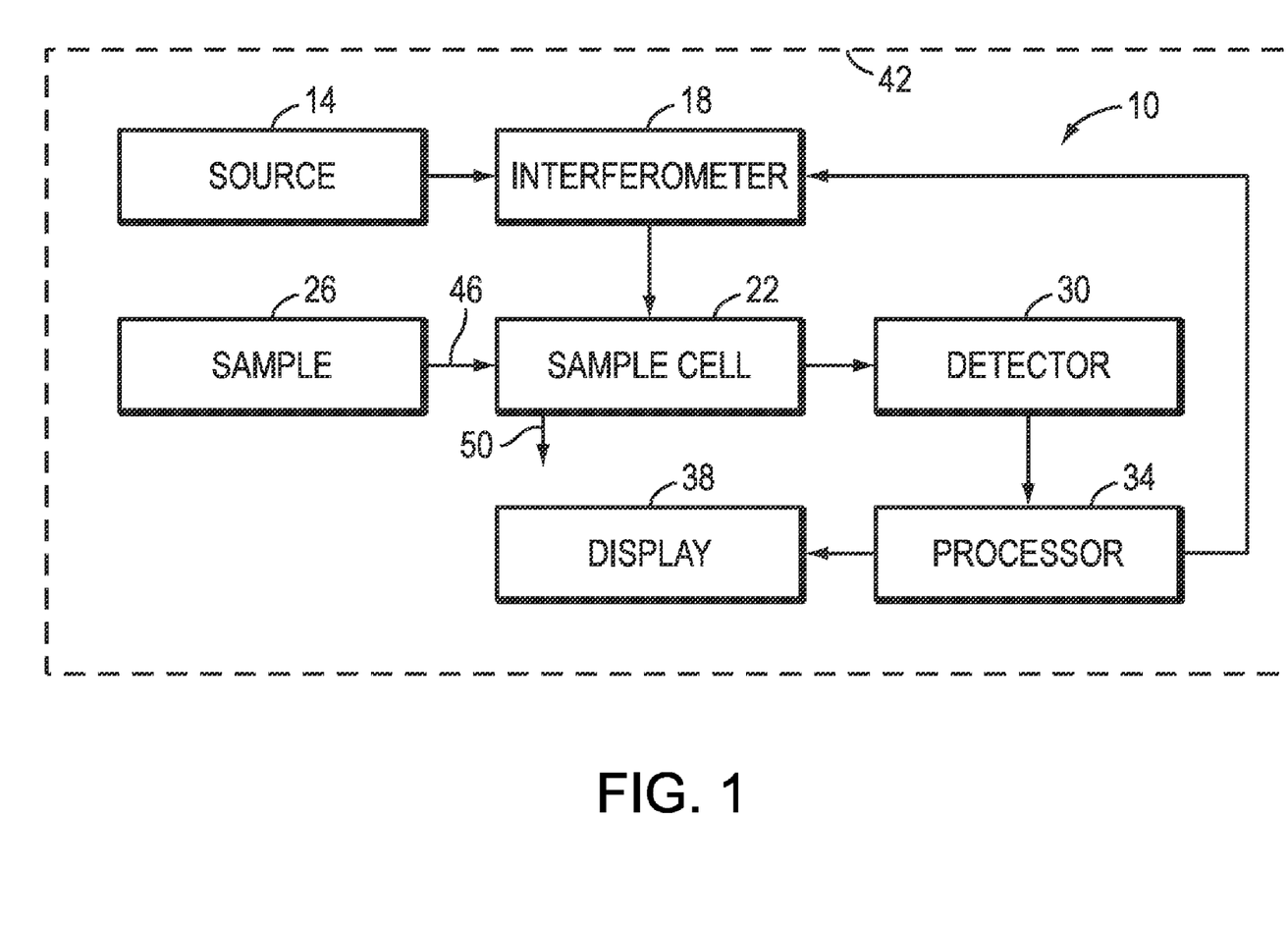
FIG. 1 depicts a block diagram of an exemplary detection system for monitoring and/or detecting a trace gas in a gas sample according to the invention.

FIG. 1 shows a block diagram of an exemplary apparatus 10 for monitoring and/or detecting a trace gas in a gas sample. The apparatus 10 can be used to detect trace amounts of substances such as sarin, tabun, soman, sulfur mustard, and VX nerve gas. In some embodiments, vapors of a solid or liquid substance can be detected. The apparatus 10 can be an absorption spectrometer and/or can be a Fourier Transform Infrared (FTIR) spectrometer. In the embodiment illustrated, the apparatus 10 includes a source 14, an interferometer 18, a sample cell 22, a source for a gas sample 26, a detector 30, a processor 34, a display 38, and a housing 42. In various embodiments, the apparatus 10 can be used to detect a trace amount of a gas in a short period of time with few, if any, false positives or negatives.

In various embodiments, the source 14 can provide a beam of radiation (e.g., an infrared beam of radiation). The source 14 can be a laser or an incoherent source. In one embodiment, the source is a glowbar, which is an inert solid heated to about 1000° C. to generate blackbody radiation. The glowbar can be formed from silicon carbide and can be electrically powered. The spectral range of the system can be between about 600 $cm^{-1}$ and about 5000 $cm^{-1}$. The resolution of the system can be 2 $cm^{-1}$ and about 4 $cm^{-1}$. In one embodiment, the detection system can record a higher resolution spectrum of a trace gas upon detection of the trace gas. The higher resolution spectrum can aid identification of the trace gas.

In various embodiments, the source 14 of radiation and the interferometer 18 can comprise a single instrument. In some embodiments, the interferometer 18 is a Michelson interferometer, commonly known in the art. In one embodiment, the interferometer 18 is a BRIK interferometer available from MKS Instruments, Inc. (Wilmington, Mass.). A BRIK interferometer can include a combiner, which splits and combines incoming radiation, a moving corner cube to modulate the radiation, a white light source used to identify the center burst, and a Vertical Cavity Surface Emitting Laser (VCSEL) to monitor the velocity of the corner cube. The BRIK interferometer can be immune to tilt and lateral motion errors, as well as to thermal variations, which can enhance the ruggedness of the interferometer.

In one embodiment, the interferometer 18 can be a module including a source of radiation, a fixed mirror, a movable mirror, an optics module, and a detector module (e.g., the detector 30). The interferometer module can measure all optical frequencies produced by its source and transmitted through a sample (e.g., the sample 26 contained within the sample ell 22). Radiation is directed to the optics module (e.g., a beamsplitter), which can split the radiation into two beams, a first signal and a second signal. The movable mirror creates a variable path length difference between these two initially, substantially identical beams of electromagnetic energy. The movable mirror is normally moved or swept at a constant velocity. After the first signal travels a different distance (in this embodiment, due to movement of the movable mirror) than the second signal, the first and second signals can be recombined by the optics module, producing a radiometric signal with an intensity that is modulated by the interference of the two beams. This interference signal is passed through the sample and measured by the detector. The presence of different samples (e.g., a solid, liquid, or gas) can modulate the intensity of the radiation as detected by the detector. The output of the detector is, therefore, a variable, time-dependent signal depending upon the optical path difference established by the relative positions of the fixed mirror and the movable mirror, as well as the modulation of the electromagnetic signal produced by the sample. This output signal can be described as an interferogram.

The interferogram can be represented as a plot of received energy intensity versus position of the movable mirror. Those skilled in the art refer to the interferogram as a signal that is a function of time. The interferogram is a function of the variable optical path difference produced by the movable mirror's displacement. Since the movable mirror's position is normally and desirably swept at a constant velocity, those skilled in the art refer to the interferogram as a "time domain" signal. The interferogram can be understood to be a summation of all the wavelengths of energy emitted by the source and passed through the sample. Using the mathematical process of Fourier Transform (FT), a computer or processor can convert the interferogram into a spectrum that is characteristic of the light absorbed or transmitted through the sample. Because individual types of molecules absorb specific wavelengths of energy, it is possible to determine the molecule(s) present in the sample based on the interferogram and the corresponding spectrum. In a similar manner, the magnitude of the energy absorbed by or transmitted through the sample can be used to determine the concentration of a molecule(s) in the sample.

In various embodiments, an interferometer is not used to form an interference signal. An absorption spectrometer is used to record an optical signal, and information about the trace species is derived from the signal transmitted through the sampling region. For example, an absorption spectrum or a differential spectrum can be used.

In various embodiments, the sample cell 22 can be a folded path and/or a multiple pass absorption cell. The sample cell 22 can include an aluminum housing enclosing a system of optical components. In some embodiments, the sample cell 22 is a folded-path optical analysis gas cell as described in U.S. Pat. No. 5,440,143, the disclosure of which is herein incorporated by reference in its entirety.

In various embodiments, the source of the sample of gas 26 can be ambient air. The sample cell 22 or a gas sampling system can collect surrounding air and introduce it to a sampling region of the sample cell 22. The sample of gas can be introduced to the sample cell 22 at a predetermined flow rate using a flow system including an inlet 46 and an outlet 50 of the sample cell 22.

In various embodiments, the detector 30 can be an infrared detector. In some embodiments, the detector 30 is a cooled detector. For example, the detector 30 can be a cryogen cooled detector (e.g., a mercury cadmium telluride (MCT) detector), a Stirling cooled detector, or a Peltier cooled detector. In one embodiment, the detector is a deuterated triglycine sulfate (DTGS) detector. In one embodiment, the detector is a 0.5 mm Stirling-cooled MCT detector with a 16-µm cutoff, which can provide the sensitivity required for detecting a trace gas. The relative responsivity (i.e., ratio of responsivity as a function of wavelength) of the Stirling-cooled MCT detector is at least 80% throughout the main wavelength region of interest (e.g., 8.3-12.5 µm). In addition, the D* value of the Stirling-cooled MCT detector can be at least $3 \times 10^{10}$ cm $Hz^{1/2}$ $W^{-1}$. The D* can be defined as the inverse of the detector noise equivalent power multiplied by the square-root of the active element area.

The processor 34 can receive signals from the detector 30 and identify a trace gas by its spectral fingerprint or provide a relative or absolute concentration for the particular material within the sample. The processor 34 can be, for example, signal processing hardware and quantitative analysis software that runs on a personal computer. The processor 34 can include a processing unit and/or memory. The processor 34 can continuously acquire and process spectra while computing the concentration of multiple gases within a sample. The processor 34 can transmit information, such as the identity of the trace gas, a spectrum of the trace gas, and/or the concentration of the trace gas, to a display 38. The processor 34 can save spectrum concentration time histories in graphical and tabular formats and measured spectrum and spectral residuals, and these can be displayed as well. The processor 34 can collect and save various other data for reprocessing or review at a later time. The display 38 can be a cathode ray tube display, light emitting diode (LED) display, flat screen display, or other suitable display known in the art.

In various embodiments, the housing 42 can be adapted to provide a detection system that is one or more of portable, rugged, and lightweight. The housing 42 can include a handle and/or can be readily secured to a transport mechanism, such as a pullcart or handtruck. The housing 42 can be rugged enough to resist misalignment of optics or breaking of components if transported and/or dropped. In various embodiments, the apparatus 10 can weigh as little as 40 pounds. In one embodiment, the apparatus 10 is entirely self-contained (e.g., includes all components in the housing 42 necessary to collect a sample, record a spectrum, process the spectrum, and display information relating to the sample).

Figure 2:
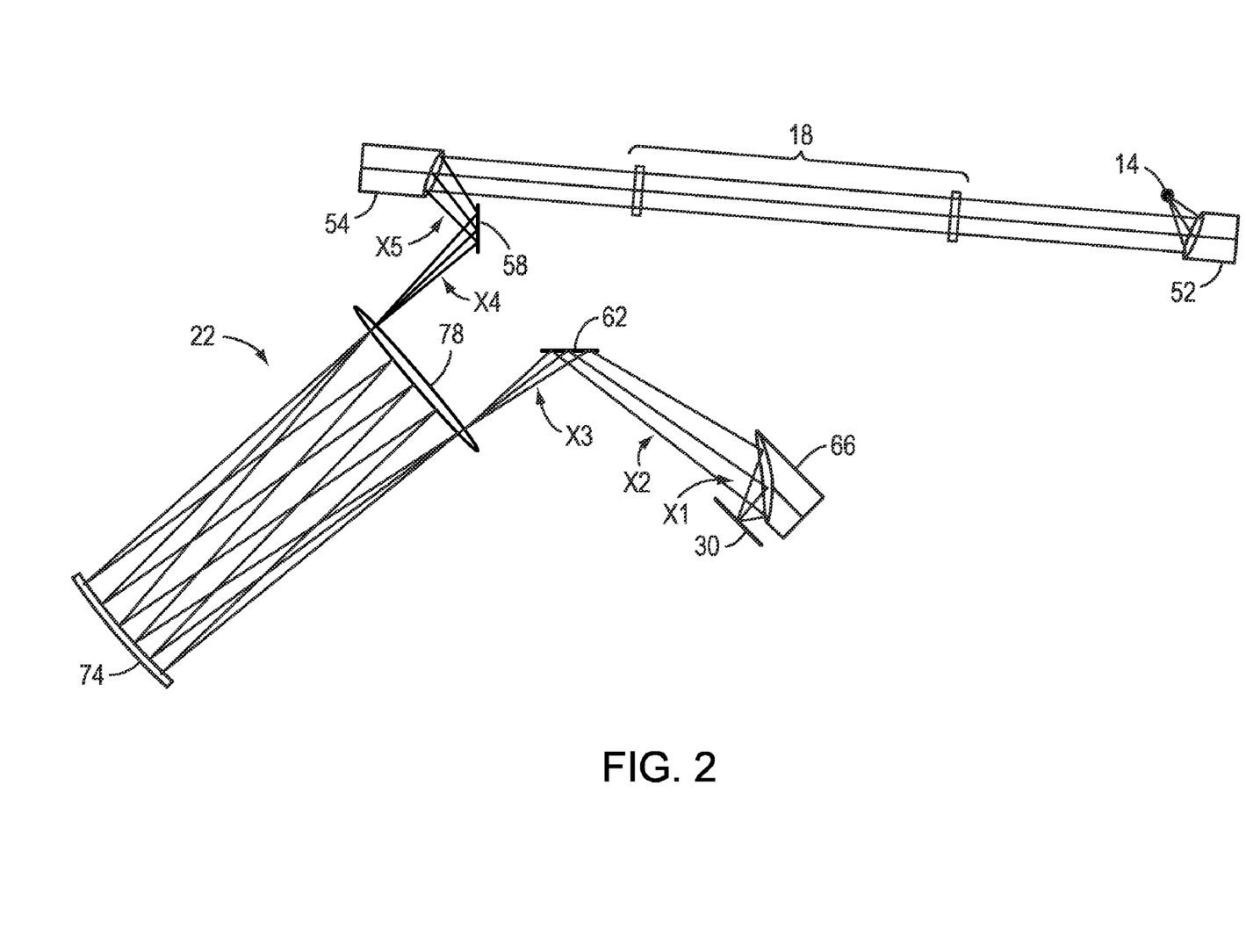
FIG. 2 shows a schematic diagram of an exemplary optical configuration according to the invention.

FIG. 2 shows an illustrative embodiment of an optical configuration that can be used with the apparatus 10. Radiation from the source 14 (e.g., a glowbar) is directed to the interferometer 18 (e.g., including a potassium bromide beamsplitter) by a first mirror 52. The beam of radiation is directed by a parabolic mirror 54 (PM) to a first folding mirror 58, and into the sample cell 22. The beam of radiation exits the sample cell and is directed by a second folding mirror 62 to a elliptic mirror 66 (EM), which directs the beam of radiation to the detector 30.

In one representative embodiment, the parabolic mirror 54 has an effective focal length of about 105.0 mm, a parent focal length of about 89.62 mm, and can have an off center value of about 74.2 mm. The diameter of the parabolic mirror 54 can be about 30.0 mm, and the angle of reflection can be about 45°.

In one embodiment, the elliptic mirror 66 can have a major semi axis of about 112.5, a minor semi-axis of about 56.09, and a tilt angle of the ellipse of about 7.11°. The diameter of the elliptic mirror 66 can be about 30.0 mm, and the angle of reflection (chief ray) can be about 75°.

In various embodiments, the first folding mirror 58 can have a diameter of about 25 mm, and the second folding mirror 62 can have a diameter of about 30 mm.

The mirrors and optics can include a gold coating, a silver coating, or an aluminum coating. In one embodiment, the elliptic and parabolic mirrors are coated with gold, and the flat folding mirrors are coated silver.

In various embodiments, the sample cell can include an objective surface 74 and a field surface 78. The objective surface 74 can be substantially spherical and concave. The field surface 78 can be concave, and positioned in a confronting relationship to the objective surface 74. The objective surface 74 can include at least one cylindrical component increasing coincidence of foci in at least one plane to maximize throughput of a beam of radiation propagating between the surfaces 74 and 78. In one embodiment, the objective surface 74 can include a plurality of substantially spherical, concave reflective objective surfaces, and each surface can include a cylindrical component increasing coincidence of foci in at least one plane to maximize throughput of the beam of radiation. The center(s) of curvature of the objective surface(s) can be positioned behind the field surface 78. By increasing coincidence of focus in at least one plane, distortion, astigmatism, spherical aberration, and coma can be better controlled, and higher throughput can be realized. Adding the cylindrical component can serve to reduce the effective radius of curvature in one plane, thus enabling light incident on the reflective surface to better approach the focus in the orthogonal plane. In one embodiment, the objective surface 74 has a cylindrical component superimposed thereupon providing different radii of curvature in two orthogonal planes. The objective surface 74 can have a contour that approaches toroidal.

The total pathlengths of the sample cell 22 can be between about 5 m and about 15 m, although longer and shorter pathlengths can be used depending on the application. In one detailed embodiment, the sample cell 22 has a total pathlength of about 10.18 m, resulting from a total number of passes of about 48 between the objective surface 74 and the field surface 78. The optics of the sample cell 22 can be optimized for 0.5-mm detector and a 1 steradian collection angle. The detector optic magnification ratio can be about 8:1. The objective surface 74 and the field surface 78 can have a gold coating with a nominal reflectance of about 98.5% between 800-1200 $cm^{-1}$. The internal volume of the sample cell can be between about 0.2 L and about 0.8 L, although larger and smaller volumes can be used depending on the application. In one detailed embodiment, the volume is about 0.45 L.

In one embodiment, the mirrors and optics used to direct the beam of radiation into and through the sample cell 22, to focus the beam of radiation on an entrance slit of the sample cell 22, and/or to direct the beam of radiation to the detector can be optimized to match the sample cell's optical characteristics, which can maximize throughput of radiation and enhance sensitivity of the detection system.

For example, in one embodiment, an optical configuration properly aligned can have an efficiency of about 88.8%. As used herein, the efficiency can be the ratio of number of rays impinging the image square to the total number of emitted rays within the angular range of emission. In one embodiment, the position of the folding mirrors 58 and 62 and the detector 30 can be adjustable, which allows one to compensate for various mechanical tolerances errors between the interferometer 18, the parabolic mirror 54, the sample cell 22, and the detector 30. In one embodiment, the following nominal (designed) optical distances can be used to optimize throughput.

Detector to elliptic mirror (X1) of about 21.39 mm.
Elliptic mirror to folding mirror (X2) of about 132.86 mm.
Folding mirror to sample cell (surface of the field mirror) (X3) of about 70.00 mm.
Sample cell path length of about 10181.93 mm.
Sample cell to folding mirror (X4) of about 70 mm.
Folding mirror to parabolic mirror (X5) of about 35 mm.

Figure 3:
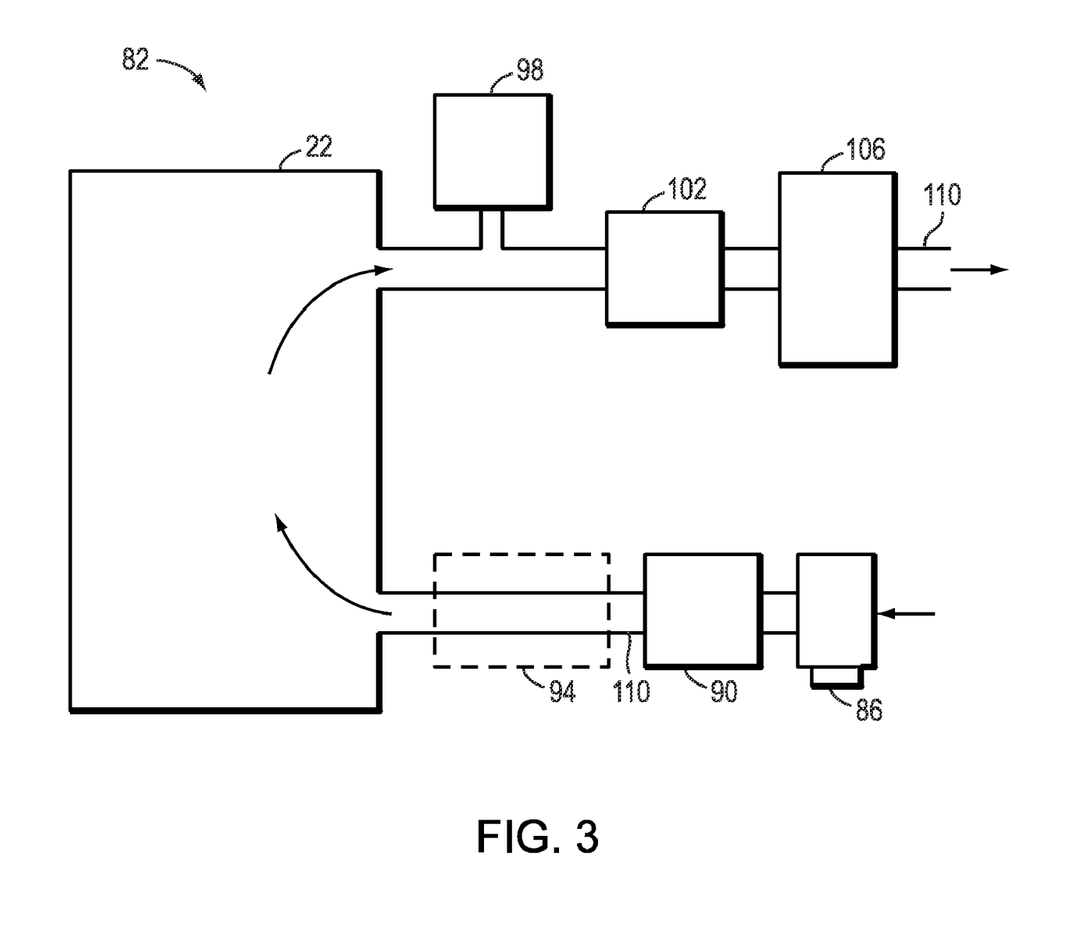
FIG. 3 shows a block diagram of an exemplary flow system for introducing a sample into a sample cell according to the invention.

FIG. 3 shows an illustrative embodiment of an exemplary flow system 82 for introducing a sample to the sample cell 22. The flow system 82 includes a filter 86, a flow sensor 90, an optional heating element 94, the gas cell 22, a pressure sensor 98, a valve 102, and a pump 106 connected by gas lines 110. Arrows show the direction of flow. One or more of the flow system 82 components can include wetted parts, such as, for example, Teflon, stainless steel, and Kalrez, to withstand decontamination temperatures and to resist the corrosive nature of CWAs and TICs.

The filter 86 can be an inline 2 μm stainless steel filter available from Mott Corporation (Farmington, Conn.). The flow sensor 90 can be a mass flow sensor including stainless steel wetted parts, e.g., a flow sensor available from McMillan Company (Georgetown, Tex.). The heating element 94 can be line heaters available from Watlow Electric Manufacturing Company (St. Louis, Mo.). The pressure sensor 98 can be a Baratron pressure sensor available from MKS Instruments (Wilmington, Mass.). The valve 102 can be stainless steel and include a Teflon o-ring, e.g., a valve available from Swagelok (Solon, Ohio). The gas lines 110 can be ⅜" diameter tubing available from Swagelok.

The pump 106 can be a "micro" diaphragm pump with a heated head. A Dia-Vac B161 pump available from Air Dimensions, Inc. (Deerfield Beach, Fla.) can be used. In one embodiment, a miniature diaphragm pump available from Hargraves Technology Corporation (Mooresville, N.C.) can be used. In the illustrative embodiment, the pump 106 can be positioned downstream from the sample cell 22 to draw air through it. As a result, any leakage in the system can be pulled away from, instead of pushed into, the analyzer to minimize the risk of contaminating the internal components of the analyzer. In addition, an unwanted product of an unintended chemical reaction involving elastomers of the pump can be prevented from entering the sample cell 22.

In various embodiments, the rate of flow through the flow system 82 can be between 2 L/min and 10 L/min, although larger and smaller flow rates can be used depending on the application. In one embodiment, the flow rate is between 3 L/min and 6 L/min. The pressure of the sample can be about 1 atm, although larger and smaller pressures can be maintained depending on the application. In some embodiments, the sample cell can be operated an elevated pressures, such as up to 4 atm. The operating temperature of the sample cell can be between about 10° C. and of about 40° C., although larger and smaller temperatures can be maintained depending on the application. In one embodiment, the detection system can include a heating element to heat the sample to between about 40° C. and of about 180° C. In one embodiment, the temperature can be increased up to about 150° C. to decontaminate the apparatus.

In various embodiments, the sample cell pathlength can be between about 5 m and about 12 m. The spacing between the field surface and the objective surface can be constrained by the gas sampling flow rate. In one embodiment, a 5.11-meter sample cell with 16 cm spacing and 32 passes can have an internal volume of about 0.2 L. In another embodiment, For the same number of passes, a 20.3 cm spacing with 32 passes can have a volume of about 0.4 L. In yet another embodiment, a 25.4 cm spacing can have a volume of about 0.6 L. A flow rate can be determined that can provide an adequate supply of "fresh" ambient gas at least every 10 seconds, although smaller sampling rates can be attained. In various embodiments, the rate of flow (e.g., between 2 L/min and 10 L/min) can be optimized to provide an optimal exchange rate of gas. For example, in one embodiment, the exchange rate of gas is at least 80% in a detection time interval of 20 seconds. In one embodiment, the gas exchange rate of is between about 80% and about 95% in a detection time interval of 10 seconds.

Pathlength/NEA ratio can be used as a metric for quantifying a detection system's sensitivity, where pathlength is the total beam path length of the sample cell measured in meters and NEA is the noise equivalent absorbance measured in absorbance units (AU). Provided that the sensitivity is limited by detection system's non-systematic errors (also called random noise, such as detector and electronic noise), the detection limit can be inversely proportional to the Pathlength/NEA ratio. For example, if the ratio were doubled, the detection limit of a particular sample in ppb or mg/m$^3$ would be halved. It is thus an appropriate quantification metric for the sensitivity performance. This metric does not take into account sensitivity enhancement due to advanced sampling techniques, such as, for example, gas pressurization and cold trapping.

Taking into account the limiting system noise, such as detector and digitization noise, Pathlength/NEA ratio can be optimized for various system configurations. Parameters that can be optimized include flow rate, sample cell volume, optical pathlength, number of passes through the sample cell, optical configuration, mirror reflectivity, mirror reflective material, and the detector used. For example, an optimum detector is one that has the highest D* value and speed (lower response time), within the constraints of size, cost and service life.

For a detector noise limited spectrometer, the sensitivity or Pathlength/NEA ratio is proportional to the D* value. Detector bandwidth can determine the maximum scan speed, which in turn determines the maximum number of data averaging that can be performed within the allowed measurement period. For a detector or electronic noise limited system, sensitivity generally increases with the square root of the number of averaged scans or, for example, the time to perform these scans. In one embodiment, a Stirling-cooled detector can provide a Pathlength/NEA sensitivity ratio of at least $1.5 \times 10^5$ m/AU. A DTGS detector can provide an inexpensive alternative due to its low cost and maintenance-free life, although it can have a lower D* value and be slower.

Figure 4:
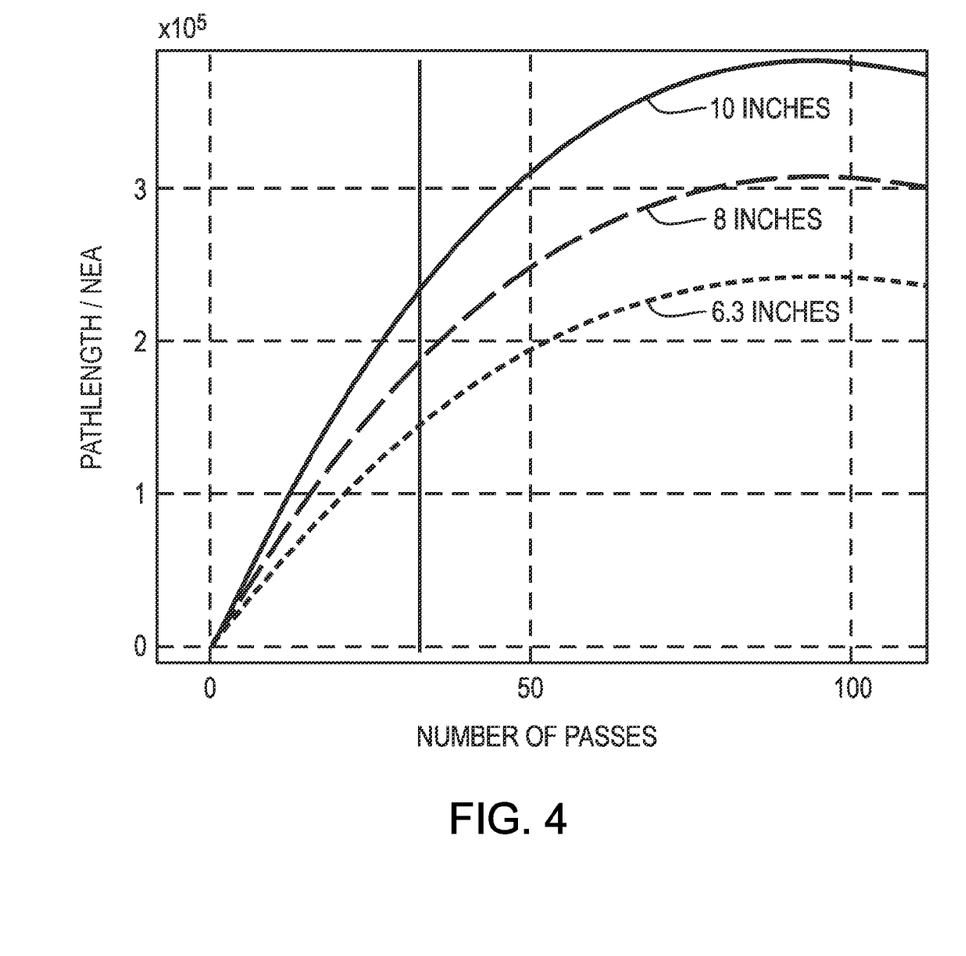
FIG. 4 is a graph of pathlength/NEA versus number of passes between optical surfaces of a sample cell according to the invention.

The Pathlength/NEA value can be determined by optimizing the distance between the field surface and the objective surface and the number of passes between these surfaces. FIG. 4 shows a graph of Pathlength/NEA as a function of mirror reflections for various surface spacings, e.g., 6.3 inches (16.0 cm), 8 inches (20.3 cm) and 10 inches (25.4 cm). As shown in FIG. 4, the maximum Pathlength/NEA values occur at about 92 passes. At 92 passes, only 25% of the light is transmitted due to reflection losses at the mirror surfaces, however. In one detailed embodiment, a sample cell has a transmittance of between about 50% and about 60%. With mirror reflectance of 98.5%, a 60% transmittance corresponds to about 32 passes, which is represented by the vertical line in FIG. 4. A 50% transmittance corresponds to about 48 passes. Table 1 shows exemplary combinations of parameters for providing a sampling system for detecting a trace gas in a sample.

TABLE 1

Exemplary combinations of parameters for providing a sampling system for detecting a trace gas in a sample.

| System | Surface spacing (cm) | Number of passes | Total pathlength (m) | Pathlength/ NEA (m/AU) | Cell volume (L) | Flow rate[1] (L/m) | Flow rate[2] (L/m) |
|---|---|---|---|---|---|---|---|
| A | 16.0 | 32 | 5.11 | $1.4 \times 10^5$ | 0.2 | 2 | 3 |
| B | 20.3 | 32 | 6.5 | $1.8 \times 10^5$ | 0.4 | 4 | 6 |
| C | 25.4 | 32 | 8.1 | $2.3 \times 10^5$ | 0.6 | 6 | 9 |
| D | 16.0 | 48 | 7.7 | $1.9 \times 10^5$ | 0.3 | 3 | 4.5 |
| E | 21.1 | 48 | 10.18 | $2.5 \times 10^5$ | 0.5 | 5 | 7.5 |
| F | 25.4 | 48 | 12.2 | $3.0 \times 10^5$ | 0.8 | 8 | 12 |

TABLE 1-continued

Exemplary combinations of parameters for providing a sampling system for detecting a trace gas in a sample.

| System | Surface spacing (cm) | Number of passes | Total pathlength (m) | Pathlength/ NEA (m/AU) | Cell volume (L) | Flow rate[1] (L/m) | Flow rate[2] (L/m) |
|---|---|---|---|---|---|---|---|

[1]Flow rate for a gas exchange rate of 80% at an interval of 10 seconds.
[2]Flow rate for a gas exchange rate of 90% at an interval of 10 seconds.

The Pathlength/NEA ratio can be translated to detection limits in mg/m$^3$ or parts per billion (ppb) of concentration. A method used for such a translation is a comparison between the expected peak absorbance magnitude and the expected NEA value. The apparatus 10 can be used to detect trace amounts of a substance such as sarin, tabun, soman, sulfur mustard, and VX nerve gas with a concentration lower than about 500 ppb. In various embodiments, the concentration can be between about 10 ppb and about 500 ppb, although higher and lower concentrations can be detected depending on the system and the application. In some embodiments, the concentration can be between 5 ppb and about 50 ppb, depending on the species. For example, the apparatus 10 is capable of detecting a trace amount of sarin with a concentration of between about 8.6 ppb and about 30 ppb; a trace amount of tabun with a concentration of between about 12.9 ppb and about 39 ppb; a trace amount of tabun with a concentration of between about 7.3 ppb and about 22.8 ppb; a trace amount of sulfur mustard with a concentration of between about 36.7 ppb and about 370.6 ppb; or a trace amount of VX nerve gas with a concentration of between about 12.9 ppb and about 43.9 ppb.

Gas renewal rate, which is a measure of the build-up of a fresh gas supply in a sample cell, can be coupled with the Pathlength/NEA ratio, resulting in a detection system response time specified as "X mg/m$^3$ (or ppb) of gas Y detected in Z seconds". The detection system response time includes the measurement time and the computation time (e.g., about 5 seconds). Table 2 shows exemplary detection system response times for various agents such as sarin, tabun, soman, sulfur mustard, and VX nerve gas.

TABLE 2

Exemplary detection system response times for trace gases measured using a detection system of the invention. All response times are in seconds.

| Trace gas | Response time for 10 ppb | Response time for 20 ppb | Response time for 30 ppb | Response time for 50 ppb |
|---|---|---|---|---|
| Sarin | 15.4 | 12 | 8.7 | 7.5 |
| Tabun | 22.6 | 12.6 | 10.2 | 8.4 |
| Soman | 13.7 | 9.6 | 8.3 | 7.2 |
| Sulfur mustard | 60 | 37.5 | 21.4 | 13.8 |
| VX nerve gas | 22.6 | 12.6 | 10.2 | 8.4 |

Figure 5:
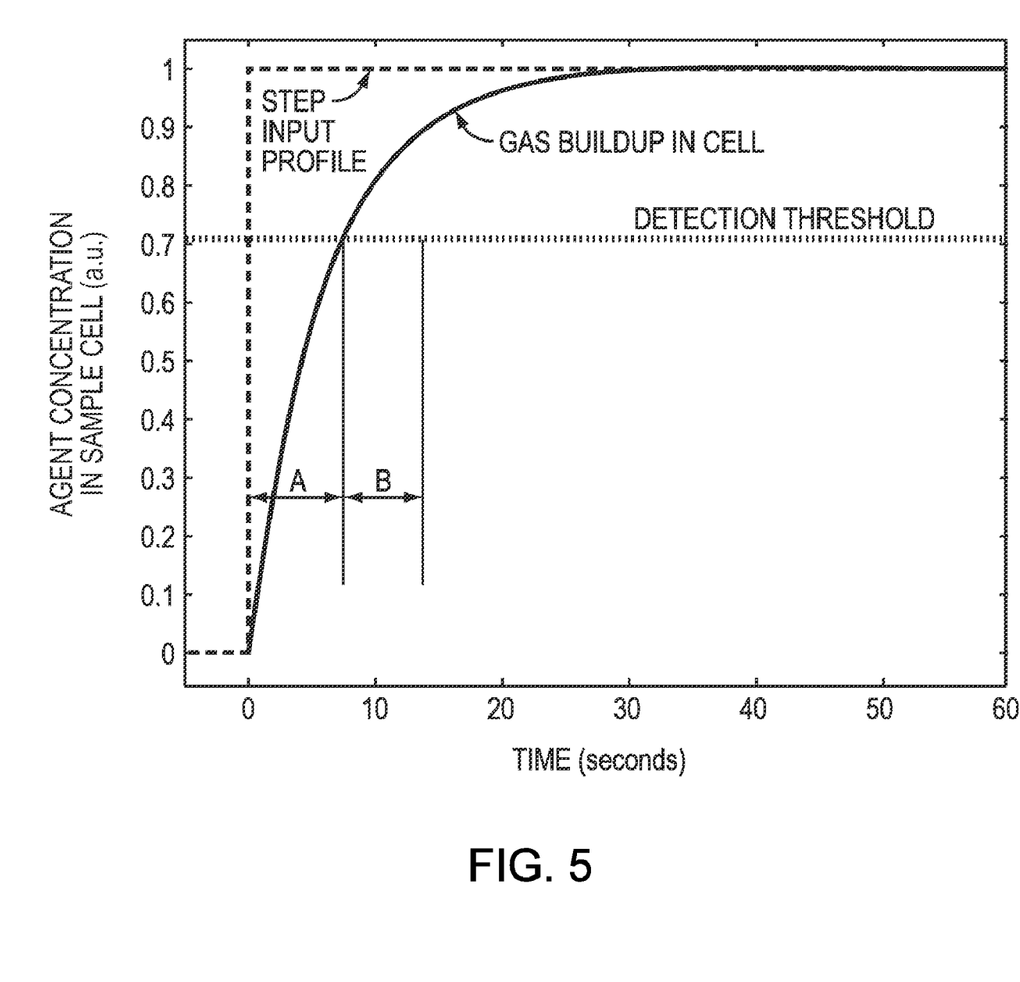
FIG. 5 is a graph of concentration of a trace gas versus time during input of the trace gas into an exemplary detection system according to the invention.

FIG. 5 is a graph of concentration of a trace gas versus time using a step profile input (e.g., the trace gas enters the sample cell at the beginning of the measurement cycle). The measurement period "A" is the time when data is collected and/or an interferogram is recorded. The computation period "B" is when the interferogram is converted to a spectrum, and a spectral analysis is performed to produce data from which alarm levels and/or concentration values can be determined.

Figure 6:
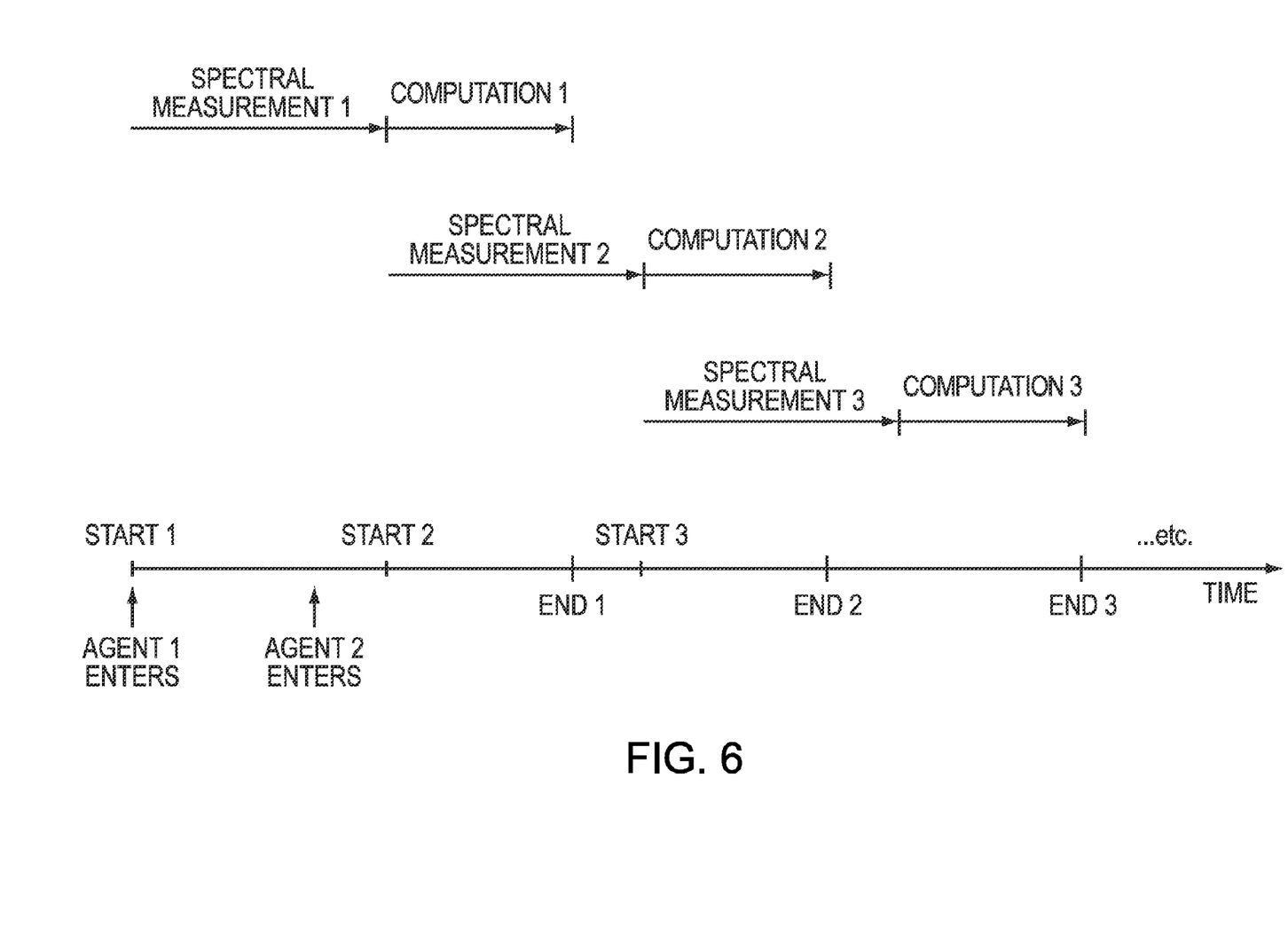
FIG. 6 shows a timeline for a series of measurements according to the invention.

FIG. 6 shows a timeline for a series of measurements. Agent 1 enters the sample cell and is detected during measurement period 1. An interferogram is analyzed during computation period 1. Agent 2 enters the sample cell during measurement period 1. If agent 2 is sufficiently strong, it can be detected during the remaining portion of measurement period 1. If agent 2 is not detectable, then it is detected during a subsequent measurement period, e.g., measurement period 2, and an interferogram is analyzed during the succeeding computation period, e.g., computation period 2.

In one embodiment, readings can be separated temporally with a fixed predetermined interval. In various embodiments, the interval can be between about 1 second and about 1 minute, although smaller or larger intervals can be used depending on the application. In some embodiments, the interval is about 5 seconds, about 10 seconds, or about 20 seconds. The response time, therefore, depends on this interval as well as when then agent is detectable by the detection system.

In various embodiments, the detection system can adapt one or more parameters based on an external factor, such as detection of a trace gas, a threat level, the time of day, the number of people in a room or building that can be affected by the agent, a particular measurement application or scenario, or a combination of the aforementioned. For example, in a high-threat condition, a smaller interval can be used to minimize detection time and maximize detectability of a trace agent. In a low threat situation, a larger interval can be used, which can preserve the detection systems lifetime and reduce the likelihood of a false alarms (either false positives or false negatives).

Furthermore, an individual measurement that exceeds a threshold level for a particular agent can trigger the detection system to decrease the interval so that additional measurements can be made in a shorter amount of time. In various embodiments, a first spectrum can be recorded at a first resolution or sensitivity. If a contaminant is detected, a second spectrum can be recorded at a higher resolution or sensitivity, respectively. Furthermore, the detector can have a standby mode, in which it operates at a higher temperature, thereby decreasing its sensitivity. When triggered by the external factor, the temperature of the detector can be decreased to improve its sensitivity.

In various embodiments, the detection system can change the number of scans based on an external factor or a perceived threat. For example, an increased number of scans can be performed to enhance the sensitivity of the detection system. In one embodiment, the detection system can operate at higher resolution while recording these additional scans. In one embodiment, each scan can include an increased number of averages or individual scans.

In various embodiments, the detection system only digitizes a low frequency region (e.g., lower than 1300 cm$^{-1}$) of the spectrum, so that the detection system can scan at a faster rate. An electronic filter or detector response function can be used to remove a higher frequency region (e.g., greater than 1300 cm$^{-1}$) so that aliasing can be prevented or minimized.

In some embodiments, the detection system can detect the presence of a trace gas in one portion of the spectrum. A second portion of the spectrum can be analyzed to confirm the presence of the trace gas and/or determine the trace gas's concentration level.

Figure 7:
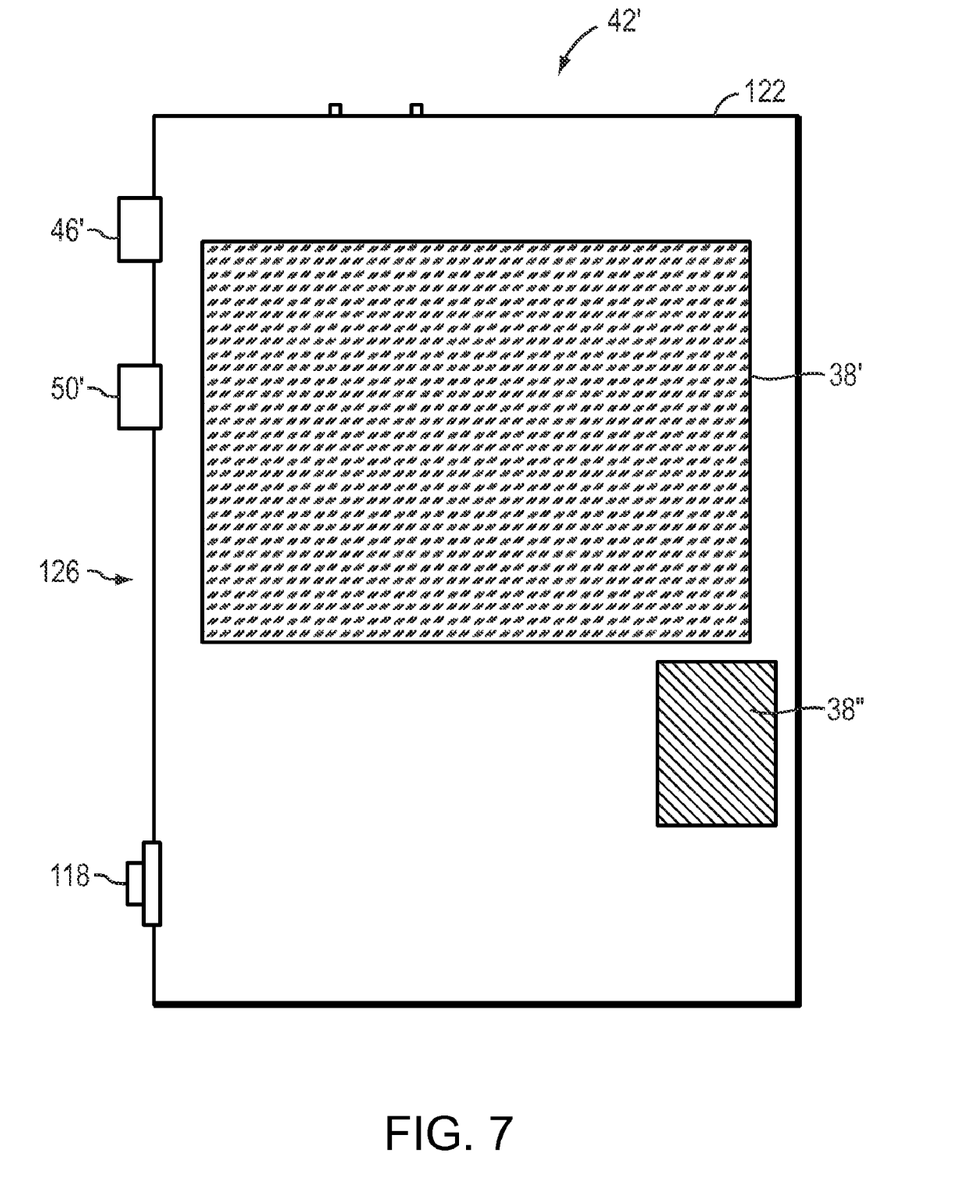
FIG. 7 depicts a plan view of an exemplary detection for monitoring and/or detecting a trace gas in a gas sample according to the invention.
Figure 8:
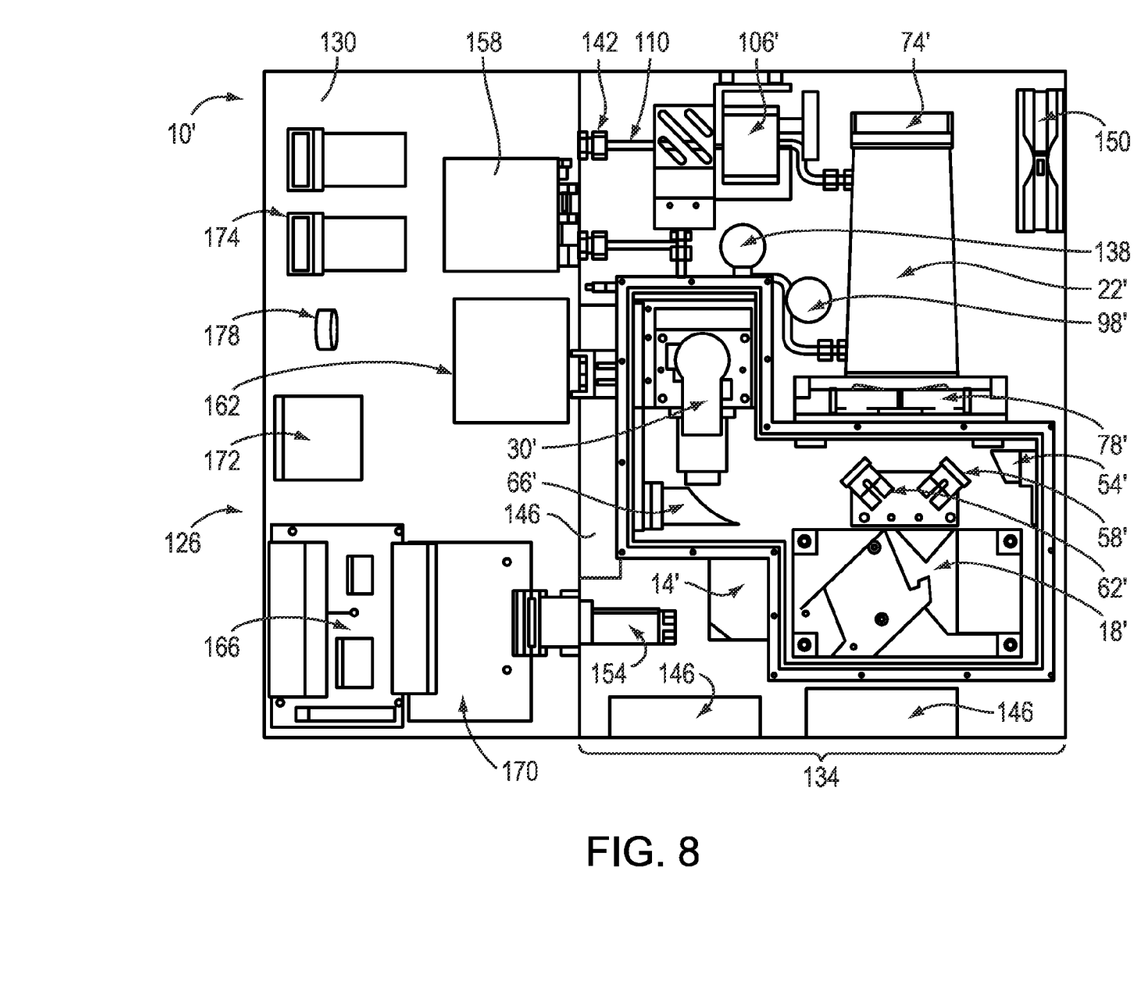
FIG. 8 shows a plan view of some components of an exemplary detection for monitoring and/or detecting a trace gas in a gas sample according to the invention.

In one embodiment, the detection system can be packaged as a compact, self-contained multiple gas analyzer. For example, the detection system can be a diagnostic tool for recording, charting, analyzing, and reporting air quality. FIGS. 7 and 8 shows an exemplary detection system for monitoring air quality, e.g., ambient air for trace gases. Referring to FIG. 7, the detection system includes a housing 42', a first display 38', a second display 38", a gas inlet 46', a gas outlet 50', and a port 118 for connecting to external devices.

The housing 42' can be a three-dimensional rectangular box including a top panel 122, side panels 126, and a bottom panel 130 (shown in FIG. 8). The top panel 122 can be hinged off a side panel 126, so that the housing 42' can be opened for service. The external surface of the top panel 122 can include the first display 38' and the second display 38" attached thereto or embedded therein. The first display 38' can be a liquid crystal display (LCD), for example, with a touchscreen display. The first display 38' can receive commands for operating the detection system and can display a graphical user interface (GUI). The second display 38" can be a light emitting diode (LED) display, for example, with a series of LEDs that light up to indicate a threat level, alarm status, and/or detection system health status. For example, the second display 38" can include a first series of green, yellow and red LEDs to indicate an alarm status, and a second series of green, yellow and red LEDs a separate to indicate sensor health status. In various embodiments, the housing 42' can define a hole for intake of ambient air. The hole can be used to introduce the sample of gas into the flow system for detection in the sample cell.

FIG. 8 shows internal views of the top panel 122 and the bottom panel 130 when the top panel 122 is hinged open. The bottom panel includes an internal chassis including an optics box 134 for housing optical components. The optics box 134 can be formed from an aluminum shell (e.g., 6061-T6). In one embodiment, the optics box 134 is a hermetically sealed box. As illustrated in FIG. 8, the optics box 134 includes a source 14', an interferometer 18', a sample cell 22', a detector 30', a parabolic mirror 54', a first folding mirror 58', a second folding mirror 62', an elliptic mirror 66', an objective surface 74', and a field surface 78'. The optics box 134 also can include a flow system including a valve 138 to regulate gas flow, a pressure sensor 98', a pump 106', and gas lines 110 and fittings 142 for making connections. Power supplies 146 for various components and a fan 150 can also be attached to the bottom panel 130. The detection system can be operated in still air, and fans 150 can maintain the internal temperature of the system. The bottom panel 130 also includes a connector 154 to interface with the top panel 122.

As illustrated in FIG. 8, the top panel 122 can include electronic components attached thereto. For example, the top panel 122 can include a data acquisition module 158, a mirror motion control module 162, a single board computer 166, a power distribution module 170, and a hard drive 172. The data acquisition module 158 can include a preamplifier, an analog-to-digital converter, and a data acquisition board. The preamplifier can amplify an analog signal received from the detector 30'. The analog signal can be converted to a digital signal using the analog-to-digital converter. The data acquisition board can be a Netburner processor board available from Netburner (San Diego, Calif.). The single board computer 166 can be an off the shelf PC motherboard running Windows and presenting a GUI to a user.

The power distribution module 170 can handle and distribute power to other modules in the system, and can implement health and status sensors used to monitor the detection system's functionality. For example, the power distribution module 170 can distribute AC power to system power supplies 146 and fans 150, and can control temperature controllers 174, e.g., Love Controls available from Dwyer Instruments, Inc. (Michigan City, Ind.). The power distribution module 170 also monitors sample cell pressure, differential pressure across the air filter, sample cell temperature, and detector temperature, A/D converts the outputs, and communicates the results back to the single board computer 166. The power distribution module 170 also can control a Stirling cooled detector's cooler motor under command from the single board computer 166. The top panel 122 also can include sample cell temperature transmitter.

Data processing can be performed using the modules attached to the top panel 122, which can enable real time analysis of data. The spectral library can include spectral fingerprints of between about 300 and about 400 gases, although more gases may be added as spectra are recorded. Data processing can be performed with a standard computer programming language, such as MATLAB or C++. The spectra recorded can be transferred to MATLAB for spectral post-processing to compute gas concentrations, spectral residuals, and/or false alarm rates. In various embodiments, the detection system can operate with fewer than about six false alarms per year. False alarms can result from noise, anomalous spectral effects, analysis code, model errors, errors in spectral library, or an unknown interferent.

The computer software can operate on a Java based platform with graphical remote control capability. It can incorporate standard services including user login, web-based GUI, alarm triggering, and/or an Ethernet interface to a client computer that may be located remote from the detection system. The computer software can perform remote health and control diagnostics. In addition, the port 118 can be used to connect the system to a stand alone computer, which can perform data processing and data analysis.

The housing 42' is designed to withstand a 50 G shock. In one embodiment, the housing 42' can have a length of about 406 mm and a width of about 559 mm. The mass the detection system can be about 20 kg. The housing 42' can be mountable on a wall, on a movable cart, or on a handtruck, and can include a handle (not shown) for carrying, either manually or using a mechanical lifting apparatus. In one embodiment, the housing can be mounted as part of an air handling system for a building. When the detector senses the presences of a contaminant, remedial measures can be taken to account for the contaminant. For example, an alarm can sound to evacuate the building, or air flow in the air handling system can be increased to sweep the contaminant away from a public area or to dilute the trace gas to an acceptable level.

In various embodiments, the detection system can be operated at an elevated temperature to decontaminate the system in the event of contamination. The system can be configured so that the sample cell and flow system can be heated to a temperature of between about 150° C. and about 200° C., while the remaining components including electronics and optical components are maintained at a temperature below about 70° C. For example, the components being heated to about 150° can be insulated from the surrounding components to prevent damage of electronics and realignment or damage of optical components. Operation of the sample cell and flow system at an elevated temperature can speed up desorption of the contaminant. In one embodiment, the detection system can be operated while the system is being decontaminated, so that progress of the decontamination can be monitored. In one embodiment, the detection system is purged with nitrogen gas or ambient air during decontamination. The gas can include moisture (e.g., a relative humidity of greater than or equal to about 30%). In various embodiments, the system can be decontaminated in less than about 2 hours and be ready to be returned to service.

In one embodiment, a concentration of a contaminant in a detection system can be determined, and if the concentration of the contaminant exceeds a contamination value, at least the sample region can be heated to a decontamination temperature to remove the contaminant. The concentration of the contaminant can be monitored while heating the sample region, and when the concentration of the contaminant reaches a decontamination value, the heating can be abated or ceased. The contamination value can be a concentration of a substance that inhibits the performance of the detection system. The decontamination value can be a concentration of the substance at which the detection system can be operated without influence from the contaminant.

In various embodiments, the sample cell of the detection system can be operated at elevated pressure. Although the Pathlength/NEA ratio may not change, the sensitivity of the detection system can be enhanced as a larger amount of a trace gas sample can be present in a sample cell having the same pathlength. This, in turn, can generate a larger absorption signal, relative to the baseline. The pressure can be elevated by increasing the flow rate while keeping the sample cell volume unchanged.

The field surface and the objective surface can be fixably mounted so that their position remains substantially unchanged when the pressure is elevated. For example, the field surface and the objective surface can be mounted on rods to hold these surfaces. In addition, the sample cell can be substantially air tight. The objective surface and the field surface in the sample cell can be bathed in the sample gas so that a positive pressure can be applied to a back surface of each of the field surface and the objective surface to prevent deformation at elevated pressure. In various embodiments, the pressure can be between 1 atm and about 10 atm. In one embodiment, the pressure is 4 atm.

In some embodiments, signals at two distinct pressures can be measured and a ratio of these signals can be taken. The ratio of signals can remove baseline noise, enhance sensitivity, and/or increase the amplitude of the absorption profile of the trace gas relative to the baseline signal.

A first signal of a beam of radiation propagating through a sample of ambient air at a first pressure in the sample cell is measured. The sample cell is pressurized with ambient air to a second pressure. A second signal of the beam of radiation propagating through the sample of ambient air is measured at the second pressure in the sample cell. The first signal and the second signal can be combined to determine a signal indicative of the presence of a trace gas. For example, the signals can be combined to yield an absorption profile for the trace gas. In one embodiment, the beam of radiation can include an interference signal. The absorption profile for the trace gas can be determined from the interference signal. In one embodiment, the first pressure is about 1 atm, and the second pressure is between about 1 atm and 10 atm. In one detailed embodiment, the first pressure is about 1 atm, and the second pressure is about 4 atm.

In various embodiments, the first signal is used as a baseline signal for the second signal because the optical alignment of the sample cell remains substantially unchanged when the pressure is increased. In some embodiments, a baseline signal is measured and used as the baseline signal for both the first signal and the second signal.

In various embodiments, the flow system can include a cold finger to trap a gaseous sample of interest by cooling it down below its saturation temperature. Many volatile materials condense at or below a temperature of −75° C. In one embodiment, a cryogenic cold trap is established in the gas outlet from the sample cell. After a specified period of time or collection period, a trapped gas or trapped gases can be rapidly vaporized or "flashed" back into the sample cell by heating them up, and a spectral measurement can be made. This technique can increase the amount of a target gas by about an order of magnitude or two, while maintaining the sample cell at atmospheric pressure. In one embodiment, continuous flow measurements are performed after an interval of time, e.g., about every 10 seconds, while flashing occurs at a longer time interval.

In various embodiments, the detection system can include a long-wave-pass filter. Noise due to the A/D converter can be on the same order of magnitude with the noise due to the detector. Incorporating a long-wave-pass filter can block the higher wavenumber region, and can improve sensitivity by reducing the digitizer dynamic range requirement through reduction of the interferogram centerburst magnitude. The dynamic range of a detector without an optical filter can be between about 600 $cm^{-1}$ and about 5000 $cm^{-1}$. Since many of the toxic substances targeted are detectable below 1500 $cm^{-1}$, the spectrum higher than 1500 $cm^{-1}$ can be eliminated using a long-wave-pass filter to gain sensitivity. For example, with a standard off-the-shelf long-wave-pass filter with a cut-off at about 1667 $cm^{-1}$, the gain in Pathlength/NEA ratio can be about 20% to about 30%. In addition, using a long-wave-pass filter can improve a detection system's signal-to-noise ratio by allow a detector to be operated at higher gain, e.g., the highest gain achievable with a particular detector. In various embodiments, a low sensitivity detector, such as a MCT detector or a DTGS detector, can be used to record a spectrum in a higher frequency region.

While the invention has been particularly shown and described with reference to specific illustrative embodiments, it should be understood that various changes in form and detail may be made without departing from the spirit and scope of the invention as defined by the appended claims.

What is claimed:

1. An apparatus capable of measuring a trace gas, comprising:
    a source of a first beam of radiation;
    an interferometer receiving the first beam of radiation from the source and forming a second beam of radiation comprising an interference signal;
    a sample cell in optical communication with the interferometer, the sample cell comprising:
        a concave reflective field surface at a first end of the sample cell; and
        a substantially spherical, concave reflective objective surface at a second end of the sample cell in a confronting relationship to the field surface, the objective surface having a cylindrical component increasing coincidence of foci in at least one plane to maximize throughput of the second beam of radiation propagating through the sample cell via multiple reflections on each of the field surface and the objective surface;
    a flow mechanism establishing a flow of a sample of gas through the sample cell;

a cooled detector in optical communication with the sample cell, the cooled detector receiving the interference signal propagating through the sample in the sample cell;

a processor in electrical communication with the cooled detector, the processor determining from the interference signal an absorption profile for a trace gas in the sample; and a housing in which the source, the interferometer, the sample cell, the cooled detector and the processor are disposed;

wherein the volume of the sample cell and the number of reflections of the second beam of radiation are optimized to detect the trace gas having a concentration of less than about 500 ppb in the sample of ambient air; and wherein the processor determines the presence of the trace gas at a first value of a detection parameter and identifies the trace gas at a second value of the detection parameter.

2. The apparatus of claim 1 wherein the detection parameter is one or more of resolution, spectral range, interval of scans, or number of scans.

3. The apparatus of claim 1 wherein the processor determines concentration of the trace gas at the second value of the detection parameter.

4. The apparatus of claim 1 wherein the detection parameter is resolution, and the processor determines the presence of the trace gas at a first resolution and identifies the trace gas at a higher resolution.

5. The apparatus of claim 1 wherein the detection parameter is spectral range, and the processor determines the presence of the trace gas in a first spectral range and identifies the trace gas in a second spectral range.

6. The apparatus of claim 1 wherein the detection parameter is interval of scans, and the processor determines the presence of the trace gas with a first interval of scans and identifies the trace gas using a lower interval of scans.

7. The apparatus of claim 1 wherein the detection parameter is number of scans, and the processor determines the presence of the trace gas using a first number of scans and identifies the trace gas using a higher number of scans.

8. A method of optically measuring a trace gas, comprising:

providing a portable absorption spectrometer comprising a sample cell including a field surface at a first end and an objective surface at a second end in a confronting relationship to form a folded path;

flowing a sample of ambient air through the sample cell;

optimizing the volume of the sample cell and the number of passes of a beam of radiation in the folded path to maximize throughput of the beam of radiation propagating in the sample cell to detect the trace gas having a concentration of less than about 500 ppb in the sample of ambient air;

detecting the presence of the trace gas at a first value of a detection parameter; and identifying the trace gas at a second value of the detection parameter.

9. The method of claim 8 wherein the detection parameter is one or more of resolution, spectral range, interval of scans, or number of scans.

10. The method of claim 8 further comprising determining concentration of the trace gas at the second value of the detection parameter.

11. A method of optically measuring a trace gas, comprising:

providing a portable absorption spectrometer comprising a sample cell including a field surface at a first end and an objective surface at a second end in a confronting relationship to form a folded path;

flowing a sample of ambient air through the sample cell;

optimizing the volume of the sample cell and the number of passes of a beam of radiation in the folded path to maximize throughput of the beam of radiation propagating in the sample cell to detect the trace gas having a concentration of less than about 500 ppb in the sample of ambient air; and varying a detection parameter of the portable absorption spectrometer based on an external factor.

12. The method of claim 11 wherein the detection parameter is one or more of resolution, spectral range, interval of scans, or number of scans.

13. The method of claim 11 wherein the external factor includes one or more of detection of the trace gas, a threat level, time of day, number of people in a room, or number of people in a building.

14. The method of claim 11 further comprising:

detecting the presence of the trace gas at a first value of the detection parameter; and identifying the trace gas at a second value of the detection parameter.

15. The method of claim 11 further comprising:

detecting the presence of the trace gas at a first value of the detection parameter; and determining concentration of the trace gas at a second value of the detection parameter.

16. The method of claim 11 further comprising using a smaller interval of scans during a high-threat condition.

* * * * *